(12) United States Patent
Blanchard

(10) Patent No.: US 8,201,561 B2
(45) Date of Patent: Jun. 19, 2012

(54) EAR TIP

(75) Inventor: Mark A. Blanchard, Lebanon, IN (US)

(73) Assignee: Klipsch Group, Inc., Indianapolis, IN (US)

( * ) Notice: Subject to any disclaimer, the term of this patent is extended or adjusted under 35 U.S.C. 154(b) by 0 days.

(21) Appl. No.: 12/592,731

(22) Filed: Dec. 2, 2009

(65) Prior Publication Data

US 2010/0084217 A1 Apr. 8, 2010

Related U.S. Application Data

(62) Division of application No. 11/584,862, filed on Oct. 23, 2006, now Pat. No. 7,681,577.

(51) Int. Cl.
| | |
|---|---|
| *A61F 5/37* | (2006.01) |
| *A61F 11/00* | (2006.01) |
| *A61F 11/06* | (2006.01) |
| *H04R 25/00* | (2006.01) |
| *H04R 25/02* | (2006.01) |
| *A61B 7/02* | (2006.01) |
| *A61N 1/00* | (2006.01) |

(52) U.S. Cl. ...... 128/864; 381/71.1; 381/71.6; 381/380; 181/128; 181/129; 181/130; 181/134; 181/135; 600/25; 607/55; 607/56; 607/57; 128/846; 128/857

(58) Field of Classification Search ............ 128/846, 128/857, 864; 181/128–135; 381/71.1, 71.6, 381/380; 600/25; 607/55–57
See application file for complete search history.

(56) References Cited

U.S. PATENT DOCUMENTS

| | | | |
|---|---|---|---|
| 177,253 | A | 5/1876 | Keats |
| 789,876 | A | 5/1905 | Pape |
| 1,556,775 | A | 10/1925 | Fensky |
| 2,246,737 | A | 6/1941 | Knudsen |
| 2,430,229 | A | 11/1947 | Kelsey |

(Continued)

FOREIGN PATENT DOCUMENTS

EP 0 567 706 10/1992

(Continued)

OTHER PUBLICATIONS

International Preliminary Report on Patentability and Written Opinion of the International Searching Authority, PCT/US2007/010723, Aug. 8, 2008.

*Primary Examiner* — Patricia Bianco
*Assistant Examiner* — Tarla Patel
(74) *Attorney, Agent, or Firm* — Krieg DeVault LLP

(57) ABSTRACT

An improved ear tip for earphones and hearing protection is provided where comfort and occlusion of the ear are of most importance. The ear tip comprises an elastomer polymer resin material molded to form the material to the shape of the ear canal. A chamber is defined having a proximal and distal end, the distal end engages the acoustic exit of the transducer, sound source or sound attenuator and the proximal end of the bore is adapted to be disposed adjacent an eardrum. The inner body attaches to a nozzle, or audio playback orifice to naturally transition the acoustics from the transducer or sound attenuator to the eardrum via the ear canal. The ear tip can have a plurality of flexible annular flanges disposed at spaced intervals of the body with decreasing circumference as the flanges transition to the proximal end. Each flange tapers in a radius or curvilinear geometry as it progresses to the end of the object.

21 Claims, 7 Drawing Sheets

U.S. PATENT DOCUMENTS

| | | | |
|---|---|---|---|
| 2,487,038 A | 11/1949 | Baum | |
| 2,521,414 A | 9/1950 | Schier | |
| 2,719,523 A | 10/1955 | Von Gierke | |
| 2,987,584 A | 6/1961 | Webber | |
| 3,061,689 A | 10/1962 | McCarrell et al. | |
| 3,080,011 A | 3/1963 | Henderson | |
| D207,216 S | 3/1967 | Geib | |
| RE26,258 E | 8/1967 | Martin | |
| 3,414,685 A | 12/1968 | Geib et al. | |
| 3,415,246 A * | 12/1968 | Hill | 128/864 |
| 3,548,118 A | 12/1970 | Hutchings | |
| 3,610,841 A | 10/1971 | Hutchings | |
| 3,618,697 A | 11/1971 | Littmann et al. | |
| 3,692,958 A | 9/1972 | Dymoke | |
| 3,865,998 A | 2/1975 | Weiss | |
| 3,993,879 A | 11/1976 | Larkin | |
| 4,006,321 A | 2/1977 | Carlson | |
| D245,202 S | 7/1977 | Asker | |
| 4,039,765 A | 8/1977 | Tichy et al. | |
| 4,122,841 A | 10/1978 | Rock et al. | |
| 4,261,432 A | 4/1981 | Gunterman | |
| D259,279 S | 5/1981 | Takeda | |
| 4,325,453 A | 4/1982 | Moussette | |
| 4,335,281 A | 6/1982 | Scott et al. | |
| 4,347,911 A | 9/1982 | Bertagna et al. | |
| 4,548,082 A | 10/1985 | Engebretson et al. | |
| 4,677,675 A | 6/1987 | Killion et al. | |
| 4,764,168 A | 8/1988 | Suh | |
| D298,356 S | 11/1988 | Falco | |
| 4,867,149 A | 9/1989 | Falco | |
| 4,870,688 A | 9/1989 | Voroba et al. | |
| 4,875,233 A | 10/1989 | Derhaag et al. | |
| 4,913,259 A | 4/1990 | Packard | |
| 4,936,411 A | 6/1990 | Leonard | |
| 5,031,219 A | 7/1991 | Ward et al. | |
| D330,761 S | 11/1992 | Falco | |
| 5,188,123 A | 2/1993 | Gardner, Jr. | |
| 5,201,007 A | 4/1993 | Ward et al. | |
| 5,288,953 A | 2/1994 | Peart | |
| 5,295,193 A | 3/1994 | Ono | |
| 5,298,692 A | 3/1994 | Ikeda et al. | |
| D353,379 S | 12/1994 | Nakamura et al. | |
| 5,487,012 A | 1/1996 | Topholm et al. | |
| 5,692,059 A | 11/1997 | Kruger | |
| 5,712,453 A | 1/1998 | Bungardt et al. | |
| 5,781,638 A | 7/1998 | Hosaka et al. | |
| 5,824,968 A | 10/1998 | Packard et al. | |
| D402,752 S | 12/1998 | Falco | |
| 5,917,918 A | 6/1999 | Callahan | |
| 5,957,136 A | 9/1999 | Magidson et al. | |
| 5,979,589 A | 11/1999 | Aceti | |
| D427,304 S | 6/2000 | Magidson et al. | |
| 6,175,633 B1 | 1/2001 | Morrill et al. | |
| 6,205,227 B1 | 3/2001 | Mahoney et al. | |
| 6,253,871 B1 | 7/2001 | Aceti | |
| 6,258,043 B1 | 7/2001 | Raviv et al. | |
| 6,359,993 B2 | 3/2002 | Brimhall | |
| D468,299 S | 1/2003 | Boesen | |
| D468,300 S | 1/2003 | Boesen | |
| D468,721 S | 1/2003 | Nguyen | |
| 6,513,621 B1 | 2/2003 | Deslauriers et al. | |
| 6,532,295 B1 | 3/2003 | Brimhall et al. | |
| D473,652 S | 4/2003 | Darley et al. | |
| 6,574,345 B1 | 6/2003 | Huang | |
| 6,643,378 B2 | 11/2003 | Schumaier | |
| 6,648,813 B2 | 11/2003 | Zilberman et al. | |
| 6,688,421 B2 | 2/2004 | Dyer et al. | |
| 6,695,093 B1 | 2/2004 | Falco | |
| 6,751,327 B1 | 6/2004 | Urso et al. | |
| D499,397 S | 12/2004 | Hlas et al. | |
| 6,920,228 B2 | 7/2005 | Redmer et al. | |
| 6,920,229 B2 | 7/2005 | Boesen | |
| 6,940,988 B1 | 9/2005 | Shennib et al. | |
| D517,054 S | 3/2006 | Yang | |
| 7,010,137 B1 | 3/2006 | Leedom et al. | |
| 7,072,476 B2 | 7/2006 | White et al. | |
| 7,079,662 B2 | 7/2006 | Niederdrank | |
| 7,082,206 B2 | 7/2006 | Mahoney et al. | |
| 7,092,543 B1 | 8/2006 | Mahoney et al. | |
| 7,107,993 B2 | 9/2006 | Magidson | |
| 7,123,733 B1 | 10/2006 | Borowsky et al. | |
| D535,644 S | 1/2007 | Drambarean et al. | |
| 7,185,655 B1 | 3/2007 | Redon | |
| D542,773 S | 5/2007 | Drambarean et al. | |
| 7,221,768 B2 | 5/2007 | Sjursen et al. | |
| D549,222 S | 8/2007 | Huang | |
| D550,201 S | 9/2007 | Drambarean et al. | |
| D550,567 S | 9/2007 | Gan et al. | |
| D550,655 S | 9/2007 | Falco | |
| 7,314,047 B2 | 1/2008 | Falco | |
| D563,945 S | 3/2008 | Johns et al. | |
| D565,022 S | 3/2008 | Belliveau et al. | |
| D567,217 S | 4/2008 | Kamo et al. | |
| D569,842 S | 5/2008 | Yang | |
| D575,767 S | 8/2008 | Lee | |
| D575,773 S | 8/2008 | Yanai | |
| D579,006 S | 10/2008 | Kim et al. | |
| 2002/0058881 A1 * | 5/2002 | Raviv et al. | 600/559 |
| 2002/0076057 A1 | 6/2002 | Voix | |
| 2003/0159878 A1 | 8/2003 | Hakansson et al. | |
| 2003/0172938 A1 | 9/2003 | Falco | |
| 2004/0047481 A1 | 3/2004 | Bauman | |
| 2004/0240691 A1 | 12/2004 | Grafenberg | |
| 2005/0018838 A1 | 1/2005 | Meunier et al. | |
| 2005/0111687 A1 | 5/2005 | Lederer | |
| 2005/0165460 A1 | 7/2005 | Erfan | |
| 2006/0050912 A1 | 3/2006 | Kidd et al. | |
| 2006/0050916 A1 | 3/2006 | Wehner | |
| 2006/0147072 A1 | 7/2006 | Sodoma | |
| 2006/0159297 A1 | 7/2006 | Wirola | |

FOREIGN PATENT DOCUMENTS

| | | |
|---|---|---|
| EP | 0 959 773 | 12/2003 |
| EP | 1 681 904 | 1/2005 |
| EP | 1 578 168 | 7/2005 |
| GB | 2 373 667 | 12/2000 |
| JP | 10023578 | 6/1996 |
| JP | 20210327 | 6/1999 |
| WO | WO 97/37593 | 4/1997 |
| WO | WO 99/04601 | 1/1999 |
| WO | WO 01/08443 | 7/2000 |
| WO | WO 2004/077924 | 3/2004 |
| WO | WO 2005/025268 | 3/2005 |
| WO | WO 2005/112503 | 5/2005 |
| WO | WO 2006/068772 | 6/2006 |

* cited by examiner

Major Axis

Minor Axis

EAR TIP

CROSS-REFERENCE TO RELATED APPLICATIONS

The present application is a divisional application of and claims priority to U.S. application Ser. No. 11/584,862 filed on Oct. 23, 2006 entitled Ear Tip and now U.S. Pat. No. 7,681,577, all of which are incorporated herein by reference in their entirety.

INTRODUCTION

The inventions disclosed and claimed herein are ear tips that come in contact with the ear canal wall, adapted for use with earphones, stethoscopes, perytympanic hearing instruments (hearing aids), headsets, and ear plugs for hearing protection, and more particularly "in ear" applications. The devices to which the ear tips can be operatively attached are generally known in the art, including earphones that can be positioned on the head or over the ear, in the ear and wires capable of operatively connecting the ear tip to an audio source such as an analog or digital audio player. Alternative uses include operative attachment to stethoscopes, hearing aids, headsets, and as ear plugs.

DETAILED DESCRIPTION OF REPRESENTATIVE EMBODIMENTS

Figure 1:
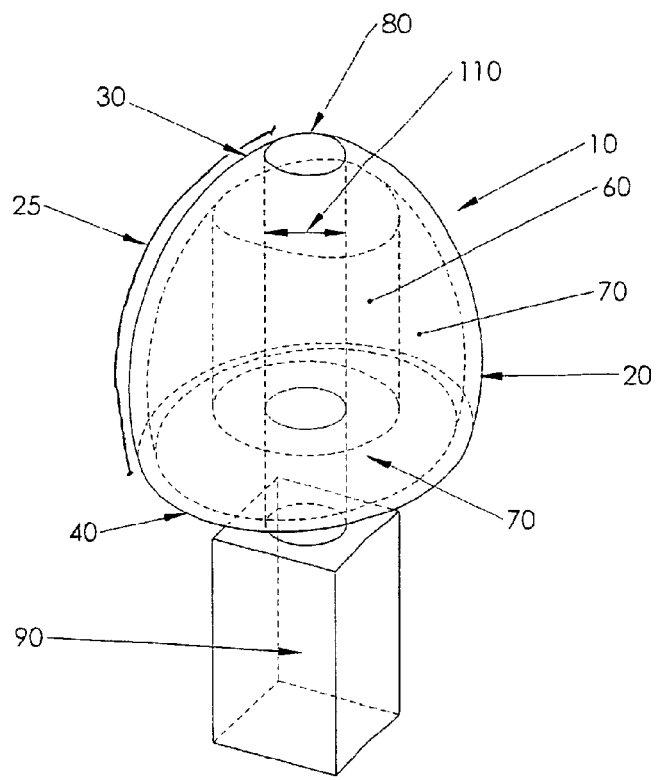
FIG. 1 shows a perspective view of one embodiment of an ear tip.

For the purpose of promoting an understanding of the principles of the invention, reference is now made to the embodiments illustrated in the drawings and specific language is used to describe the same. No limitation of the scope of the invention is intended. Alterations and modifications to the illustrated devices, and other applications of the principles of the invention as illustrated herein are contemplated as would normally occur to one skilled in the art to which the invention relates.

Figure 2:
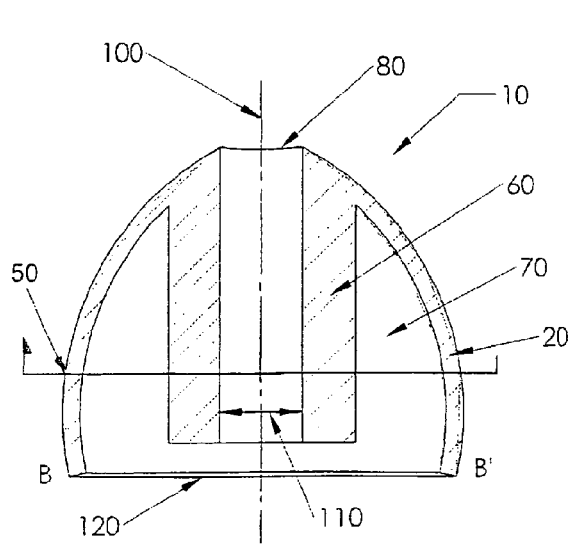
FIG. 2. shows a longitudinal cross-section of the ear tip shown in FIG. 1 taken along the major axis.
Figure 3:
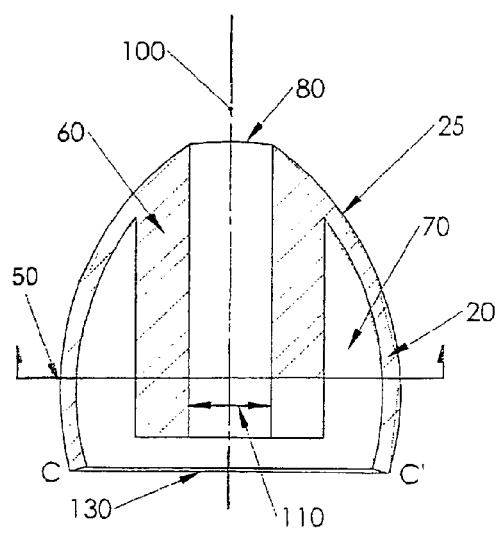
FIG. 3 shows a longitudinal cross-section of the ear tip shown in FIG. 1 taken along the minor axis.
Figure 4:
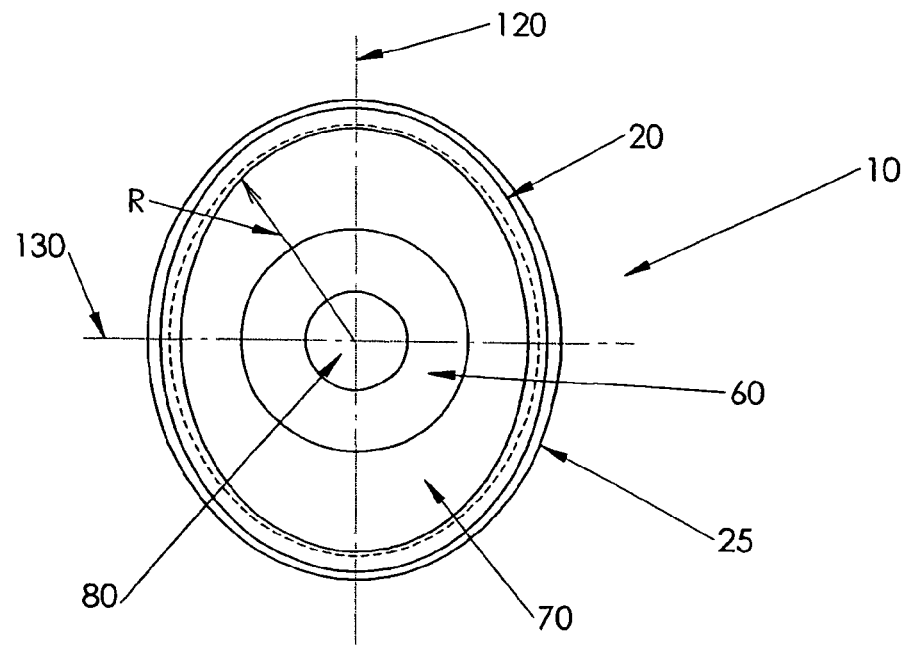
FIG. 4 shows a lateral cross-section of an embodiment having an elliptical cross-section.

As shown in FIGS. 1 and 2, the ear tip 10 has an annular flange 20 having a first end 30, a second end 40, at least a partially non-circular cross section 50 (shown for example in FIGS. 2-4). An inner body 60 extends from the first end 30 toward the second end 40 within a chamber 70. An acoustic channel 80 extends through the inner body 60 to connect operatively the sound source or sound attenuator 90 to the ear drum (not shown).

An inner body 60 is formed as part of the flange 20. The inner body 60 is positioned so that its longitudinal axis is generally concentric with the longitudinal axis of the flange 20 (i.e. along axis 100 as shown on FIGS. 2 and 3). The acoustic channel 80 extends through the inner body 60 and the first end 30. A transducer (not shown) may be positioned within or without the chamber 70. The inner body 60 may be formed integrally with the flange 20 or as a separate piece which is then attached to the flange 20.

The inner diameter 110 of the acoustic channel 80 is sized to secure an acoustic connection from a sound source or sound attenuator 90. The acoustic channel 80 in one version has a diameter of about 1.26 millimeters. In another version, the acoustic channel 80 has a diameter of about 1.40 millimeters. Variations to the diameter of the acoustic channel 80 can be made without varying from the scope of the invention disclosed and claimed herein.

The exterior surface 25 of the flange 20 tapers to the first end 30 from the second end 40. The arc of the taper can be constant or variable. In one version the radius is 5 millimeters. In another version, the radius is 9 millimeters. In other embodiments, the flange 20 has a generally conical three-dimensional shape. Again, variations in the arc or radius of the taper can be made without varying from the scope of the invention disclosed and claimed herein.

Referring to FIGS. 2 and 3, the ear tip 10 has a major axis 120 along B-B' and minor axis 130 along C-C'. The major axis 120 is longer than the minor axis 130. The minor axis 130 has a length from about 6 millimeters to about 10 millimeters. The major axis 120 has a length from about 9 millimeters to about 15 millimeters. The ratio of the length of the major axis 120 relative to the minor axis 130 can range from about 1.1:1 to about 3:1. The lengths of the axes can be varied without departing from the scope of the inventions disclosed and claimed herein.

Figure 5:
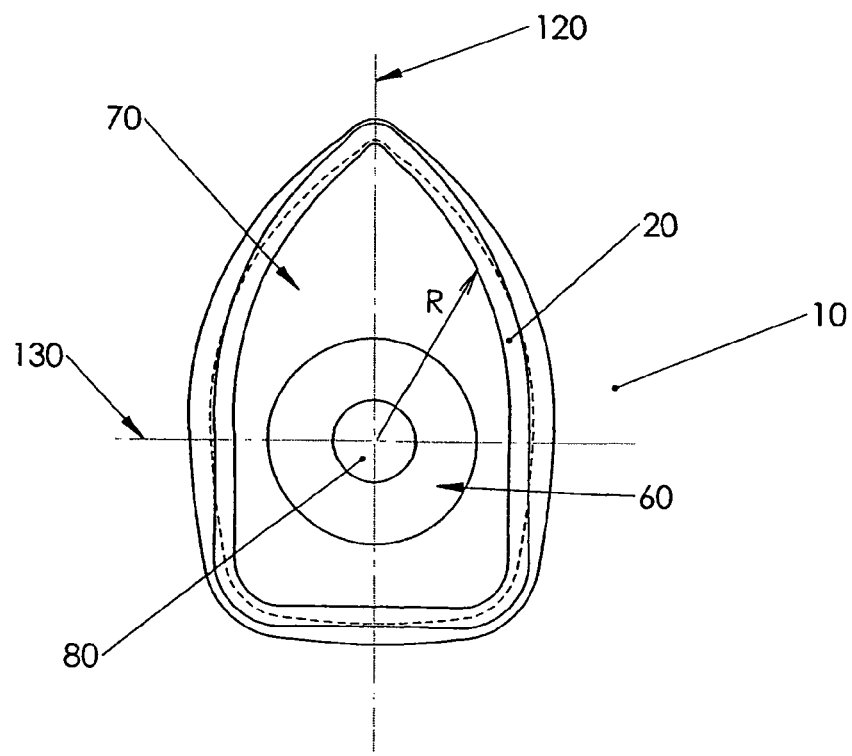
FIG. 5 shows a lateral cross-section of an embodiment having a generally triangular cross-section.
Figure 6:
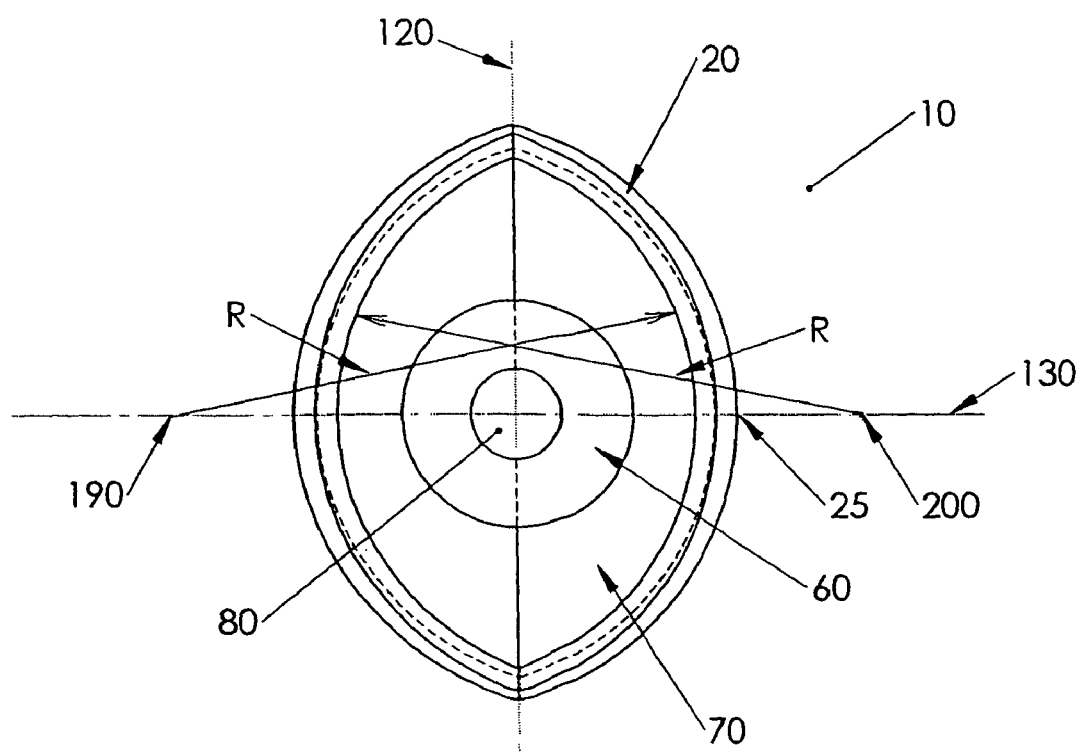
FIG. 6 shows a lateral cross-section of an embodiment having a clamshell shaped cross-section.

FIGS. 4-6 show several embodiments having different shaped lateral cross-sections. FIG. 4 shows a flange 20 having a generally elliptical cross-section 50. The major axis 120 and minor axis 130 are shown. Radius "R" will decrease as it arcs from the major axis 120 to the minor axis 130 according to known mathematical equations for ellipses $[(x^2/a^2)+(y^2/b^2)=1]$. One can infinitely vary the radius "R" or the generally elliptical shape of the inventions without departing from the scope thereof as disclosed and claimed.

FIG. 5 shows another embodiment with a flange 20 having a generally triangular shaped lateral cross-section. This generally triangular shaped lateral cross-section can also be referred to as a tri-oval shape. The inner body 60 defines an acoustic channel 80. Taken from the axis of the acoustic channel 80, radius R varies in length as it arcs from the minor axis 130 to the major axis 120. Sections of the cross-section can have generally non-radial lineal geometries in varying length (FIG. 5).

FIG. 6 shows another embodiment with a flange 20 having a generally clamshell shaped lateral cross-section. This clamshell shape can be described as taking a longitudinal cross-section along the major axis 120 thereby separating the flange 20 into two halves having radii "R" based on center points 190, 200 outside the acoustic channel 80. Alternatively the center points 190, 200 can be inside the chamber 70 or acoustic channel 80. FIG. 5 shows another embodiment with a flange 20 having a generally triangular shaped lateral cross-section. This generally triangular shaped lateral cross-section can also be referred to as a tri-oval shape. The inner body 60 defines an acoustic channel 80. Taken from the axis of the acoustic channel 80, radius R varies in length as it arcs from the minor axis 130 to the major axis 120. Sections of the cross-section can have generally non-radial lineal geometries in varying length (FIG. 5).

FIG. 6 shows another embodiment with a flange 20 having a generally clamshell shaped lateral cross-section. This clamshell shape can be described as taking a longitudinal cross-section along the major axis 120 thereby separating the flange 20 into two halves having radii "R" based on center points 190, 200 outside the acoustic channel 80. Alternatively the center points 190, 200 can be inside the chamber 70 or acoustic channel 80.

Figure 7:
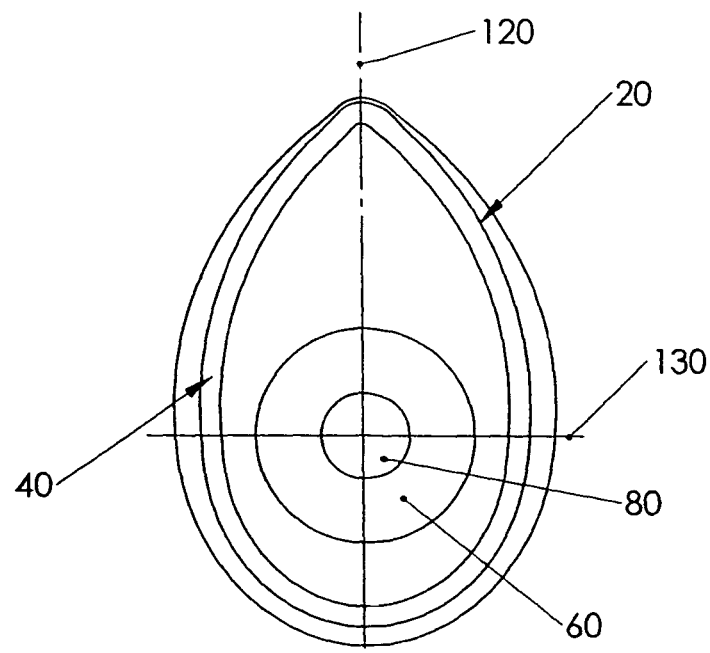
FIG. 7 shows a lateral cross-section of the ear tip having a teardrop cross-section.

Referring to FIG. 7, the flange 20 has a lateral cross-section having a generally teardrop shape. Alternatively, the lateral cross-section of the flange 20 can be generally oval, elliptical, or triangular (FIGS. 4 and 5). The flange 20 can have a cross-section having a substantially uniform arc as it extends from the minor axis 130 to the major axis 120. In another version, the flange 20 has a cross-section has a variable arc as it extends from the minor axis 130 to the major axis 120. In another variation, the flange 20 has a cross-section having a generally increasing radius as it extends from the minor axis 130 to the major axis 120.

Figure 8:
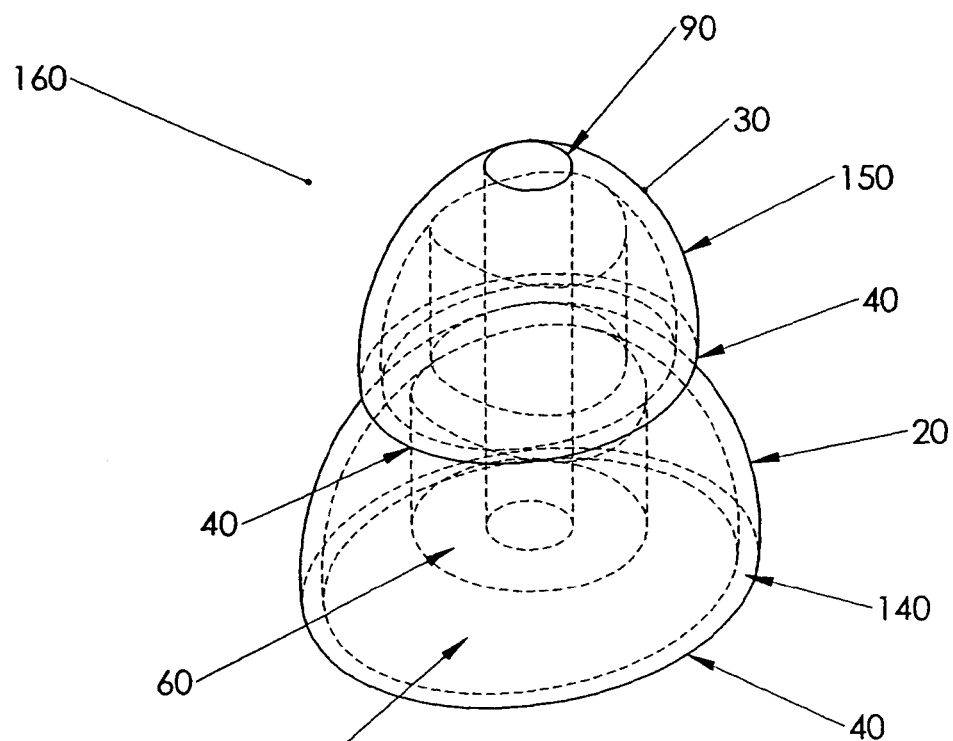
FIG. 8 shows a perspective view of another embodiment of the invention having two flanges.
Figure 9:
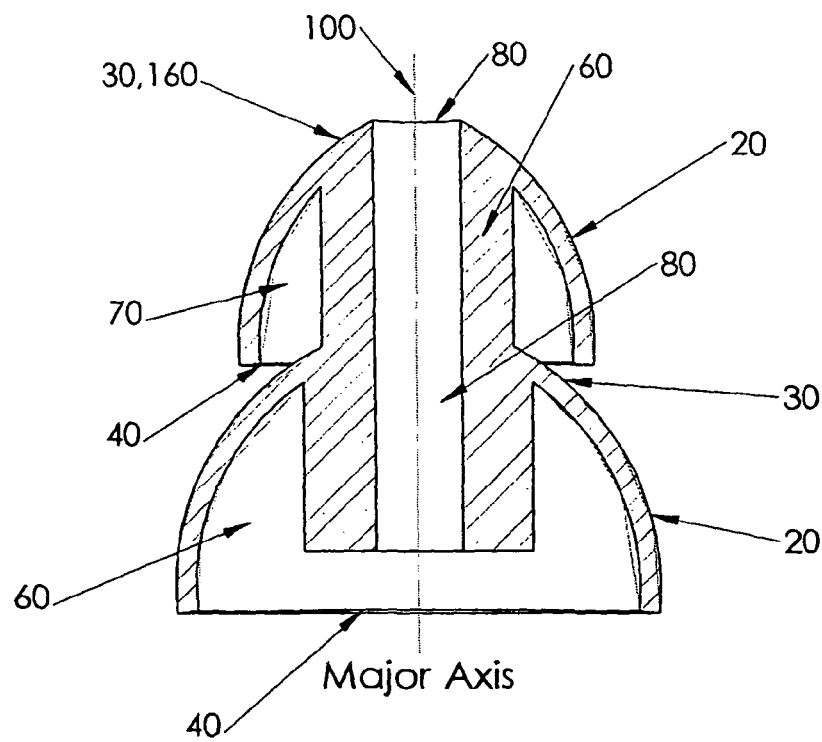
FIG. 9 shows a longitudinal cross-section of the embodiment shown in FIG. 5 taken along the major axis.
Figure 10:
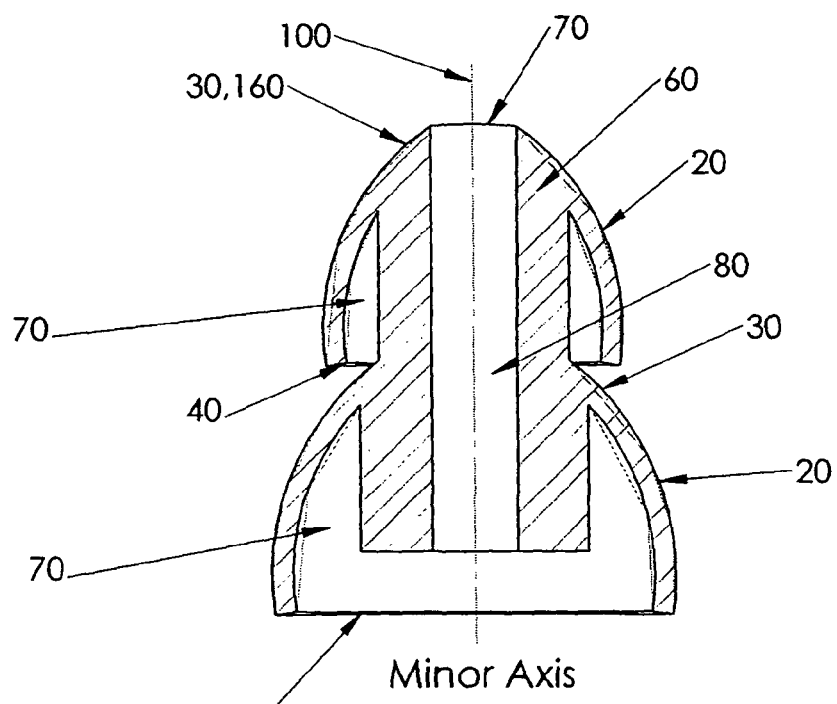
FIG. 10 shows a longitudinal cross-section of the embodiment shown in FIG. 5 taken along the minor axis.

Single flange ear tips 10 attenuate ambient noise by about 5 to about 15 dB. For additional noise isolation, multiple flanges 140, 150 can be used to yield attenuation up to about 32 dB. FIGS. 8-10 show a perspective view of an embodiment having a first flange 140 and a second flange 150 positioned along a common longitudinal axis (not shown). More than two flanges 140, 150 may be used without departing from the scope of the inventions disclosed and claimed.

The flanges 140, 150 have generally decreasing diameters as the flanges 140, 150 transition to an insertable end 160. The insertable end 160 is that portion of the ear tip 10 that is inserted the furthest into the ear canal. The flanges 140, 150 can be of single piece construction or multiple piece construction. For the embodiments having multiple flanges 140, 150, the inner body 60 can have an acoustic channel 80 extending through it. The inner body 60 traverses at least part of the length of both flanges 140, 150 as shown in FIG. 8-10. Each of the flanges 140, 150 has a first end 30 and a second end 40. At least one of the flanges 140, 150 has a partially non-circular cross section as described above with respect to the embodiment having a single flange 20. Each of the flanges 140, 150 defines a chamber 70.

Figure 11:
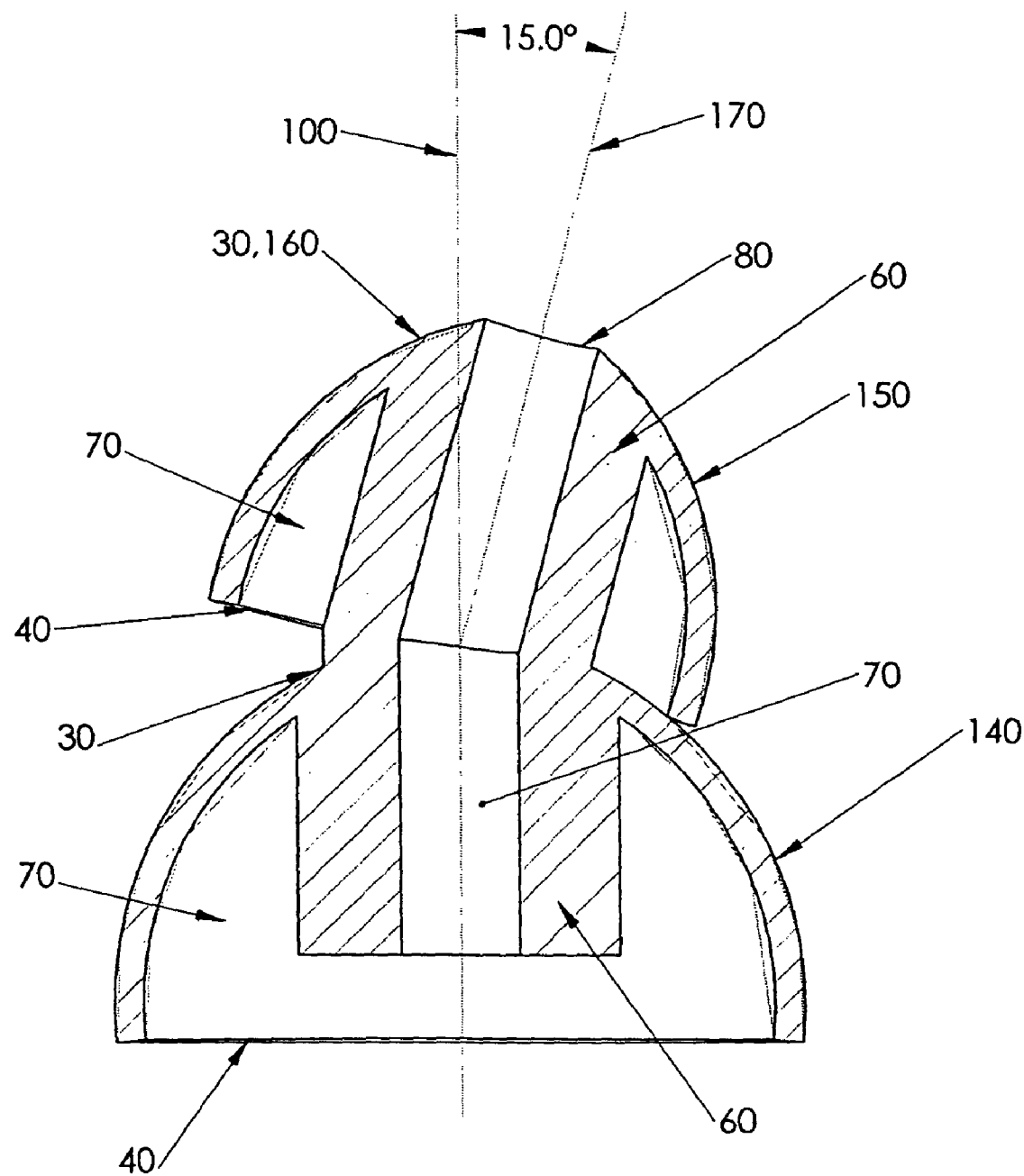
FIG. 11 shows another embodiment in which a first flange is positioned relative to a second flange at a 15° angle.

In one embodiment having two flanges (FIG. 11), the second flange 150 has a longitudinal axis 170 angled about 15 to about 30 degrees from the longitudinal axis 100 of flange 140. The deflection of the second flange 150 with respect to the first flange 140 can comprise a compound angle that is an angle of 15° in the x-axis and 15° in the y-axis or any combination thereof. Referring to FIGS. 9 and 10, in another embodiment, the longitudinal axis 100 of both flanges 140, 150 are common. In embodiments having multiple flanges 140, 150 (FIGS. 8-10), the flanges 140, 150 may have the same or different shaped lateral cross-sections, including oval, elliptical, triangular or teardrop shaped.

Rigid, deformable, flexible, elastic or resilient materials provide flexibility in sizing the ear bud, comfort, audio quality and durability. In one embodiment, the flange is a polymer. In another embodiment, the flange is an elastomeric polymer. In another embodiment the flange 20 is comprised of ABS plastic or polycarbonate plastic.

In single and multiple flange embodiments, the inner body 60 will have sufficient thickness and stiffness to resist deformation when it is connected to a sound source and when the ear tip 10 is inserted into an ear.

Figure 12:
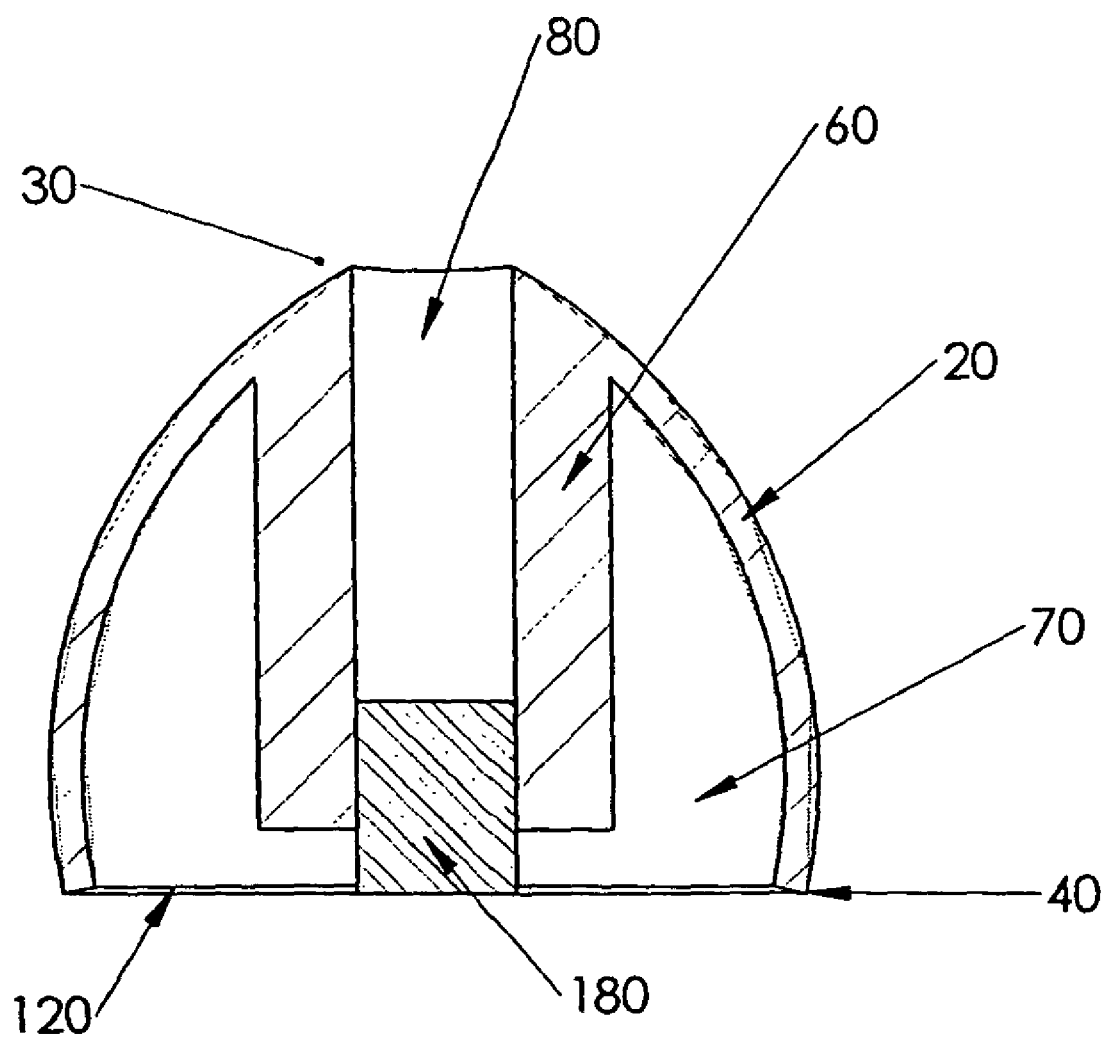
FIG. 12 shows a longitudinal cross-section of an embodiment having an insert.

As shown in FIG. 12, a removable or fixed insert 180 may be provided to plug the acoustic channel 80 thereby rendering the invention an ear plug. The insert 180 may be formed integrally with the inner body 60 to become either a homogeneous or non-homogeneous solid body.

The invention has been illustrated and described in detail in the drawings and foregoing description. The same is illustrative and not restrictive in character. Only the preferred embodiments have been shown and described. All changes and modifications that come within the spirit of the inventions are desired to be protected.

While the use of words such as preferable, preferably, preferred or more preferred utilized in the description indicate that the feature so described may be more desirable, such feature(s) may not be necessary. Embodiments lacking the same are within the scope of the invention as defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

I claim:

1. An ear tip, comprising:
   a first annular flange having a base end extending upwardly toward an upper end, wherein the first annular flange has a first non-circular lateral cross section running from approximately the base end to the upper end, the first non-circular lateral cross-section has a first major axis and a first minor axis, the first major axis having a greater length than the first minor axis thereby defining the first annular flange as having a elliptically shaped non-circular lateral cross section running from the base end to the upper end;
   a second annular flange having a second base end extending upwardly toward a second upper end, wherein the upper end of the first annular flange is positioned such that the second base end of the second annular flange is oriented in a stacked relationship with the upper end of the first annular flange, wherein the second base end of the second annular flange is connected with the upper end of the first annular flange; and
   wherein at least a portion of the second annular flange is configured to at least partially occlude an ear canal from ambient noise thereby creating at least a partial air seal in the ear canal.

2. The ear tip of claim 1, wherein the second annular flange has a second non-circular lateral cross section running from approximately the second upper end to the second base end, the second non-circular lateral cross-section has a second major axis and a second minor axis, the second major axis having a greater length than the second minor axis thereby defining the second annular flange having an elliptically shaped non-circular lateral cross section running from the second upper end to the second base end.

3. The ear tip of claim 1, wherein the first annular flange tapers outwardly toward the base end from the upper end such that the upper end has a smaller lateral cross-section than the base end.

4. The ear tip of claim 3, wherein an inner body extends internally from the second upper end of the second annular flange downwardly toward the base end of the first annular flange within the first annular flange, and an acoustic channel extends through the inner body.

5. The ear tip of claim 4, wherein the acoustic channel extends through the entire inner body and an outer portion of the inner body does not touch select internal portions of the first and second annular flanges.

6. The ear tip of claim 5, wherein the inner body terminates prior to reaching the base end of the first annular flange.

7. The ear tip of claim 1, further comprising an acoustic channel extending through an inner body, wherein the inner body is located within a first hollow interior defined by the first annular flange and a second hollow interior defined by the second annular flange.

8. The ear tip of claim 7, wherein the inner body connects the first annular flange with the second annular flange such that the second base end of the second annular flange is positioned at approximately the upper end of the first annular flange.

9. The ear tip of claim 1, wherein the first annular flange and the second annular flange lie along a common longitudinal axis.

10. The ear tip of claim 1, wherein the second annular flange has a first longitudinal axis angled at a predetermined angle with respect to a second longitudinal axis of the first annular flange.

11. The ear tip of claim 10, wherein the predetermined angle is between approximately 15° and 30°.

12. An ear tip, comprising:
a upper annular flange stacked on top of a lower annular flange, wherein the upper annular flange has a non-circular lateral cross section running from a first upper end to a first base end, the upper annular flange tapering outwardly from the first upper end to the first base end, wherein the upper annular flange is sized and configured to fit within an ear canal to at least partially occlude the ear canal from receipt of ambient noise;
an inner body extending internally from the first upper end of the upper annular flange downwardly and into a first hollow interior defined by the upper annular flange and into the lower annular flange, wherein an interior portion of the inner body connects the upper annular flange with the lower annular flange to allow the upper and lower annular flanges to be stacked on top of one another; and
an acoustic channel extending through the inner body such that sound from a sound source configured to be connected with a lower end of the inner body can pass into the ear canal.

13. The ear tip of claim 12, wherein the inner body extends into a second hollow interior defined by the lower annular flange.

14. The ear tip of claim 13, wherein the inner body terminates prior to reaching a second base end of the lower annular flange such that the inner body is positioned entirely within the second hollow interior.

15. The ear tip of claim 12, wherein the lower annular flange has a non-circular lateral cross-section running from a second upper end to a second base end, the lower annular flange tapering outwardly from the second upper end to the second base end, wherein at least a portion of the lower annular flange is sized and configured to fit within the ear canal to occlude the ear canal from receipt of ambient noise.

16. The ear tip of claim 12, wherein the inner body connects the second upper end of the lower annular flange with the first upper end of the upper annular flange.

17. The ear tip of claim 12, wherein the upper annular flange and lower annular flange are oriented along an identical longitudinal axis with one another.

18. The ear tip of claim 12, wherein the upper annular flange is angled at a predetermined angle in relation to the lower annular flange.

19. The ear tip of claim 18, wherein the predetermined angle is about 15° to 30° offset from a longitudinal axis extending through a central portion of the lower annular flange.

20. The ear tip of claim 12, wherein the non-circular lateral cross section may form a shape selected from a group of shapes including an elliptical shape, an oval shape, a triangular shape, or a teardrop shape.

21. An ear tip, comprising:
a first annular flange having a first end and a second end, where the first annular flange has a non-circular lateral cross section running from approximately the first end to the second end, the non-circular lateral cross section has a first major axis and a minor axis, the first major axis having a greater length than the first minor axis, the first annular flange tapering to the first end from the second end;
a second annular flange having a third end and a fourth end, where the second annular flange has a non-circular lateral cross section running from approximately the third end to the fourth end, the non-circular lateral cross section has a second major axis and a second minor axis, the second major axis having a greater length than the second minor axis, the second annular flange tapering to the third end from the fourth end;
an inner body extending internally from the first end within a first hollow interior defined by the first annular flange and terminating at a point within a second hollow interior defined by the second annular flange, wherein at least a portion of the inner body connects the first annular flange with the second annular flange such that said first and second annular flanges are oriented in a stacked relationship with one another; and
an acoustic channel extending through the inner body, wherein the first annular flange is configured and arranged to at least partially occlude an ear canal from ambient noise and creates at least a partial air seal in the ear canal and the acoustic channel is configured to allow the passage of sound into the ear canal when the inner body is connected with a sound source.

* * * * *